United States Patent [19]

VandenBerg

[11] Patent Number: Plant 7,407

[45] Date of Patent: Dec. 25, 1990

[54] CHRYSANTHEMUM PLANT NAMED MOMENTO

[75] Inventor: Cornelis P. VandenBerg, Salinas, Calif.

[73] Assignee: Yoder Brothers, Inc., Barberton, Ohio

[21] Appl. No.: 435,816

[22] Filed: Nov. 14, 1989

[51] Int. Cl.[5] ..... A01H 5/00

[52] U.S. Cl. ..... Plt./78

[58] Field of Search ..... Plt./78

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Momento particularly characterized by its flat capitulum form; decorative capitulum type; yellow ray floret color; diameter across face of capitulum of up to 7 cm at maturity; uniform eight week photoperiodic flowering response to short days; peduncle length ranging from 10 to 20 cm on open, terminal sprays; tall plant height when grown as a single stem spray cut mum; and excellent tolerance to low temperatures for bud initiation and flower development.

3 Drawing Sheets

The present invention comprises a new and distinct cultivar of Chrysanthemum, botanically known as *Dendranthema grandiflora,* and referred to by the cultivar name Momento.

Momento, identified as 85-247003, was originated from a cross made by Cornelis P. VandenBerg in a controlled breeding program in Salinas, Calif. in 1984.

The female parent of Momento was an unnamed seedling identified as 81-651001, and described as a spray cut mum with yellow flower color, decorative capitulum type, medium height and nine week photoperiodic flowering response to short days. The male parent of Momento was an unnamed seedling, identified as 81-080001 and described as a spray cut mum with white flower color, decorative capitulum type, tall plant height and ten week photoperiodic flowering response to short days.

Momento was discovered and selected as one flowering plant within the progeny of the stated cross by Cornelis P. VandenBerg in March 1986, in a controlled environment in Salinas, Calif.

The first act of asexual reproduction of Momento was accomplished when vegetative cuttings were taken from the initial selection in May 1986, in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Momento are firmly fixed and are retained through successive generations of asexual reproduction.

Momento has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. The low temperature tolerance of the new variety as noted below was determined in repeated flowerings in Bogota, Colombia.

The following traits have been repeatedly observed and are determined to be basic characteristics of Momento, which, in combination, distinguish this Chrysanthemum as a new and distinct cultivar:

1. Flat capitulum form.
2. Decorative capitulum type.
3. Yellow ray floret color.
4. Diameter across face of capitulum of up to 7 cm at maturity.
5. Uniform eight week photoperiodic flowering response to short days.
6. Peduncle length ranging from 10 to 20 cm on open, terminal sprays.
7. Tall plant height, requiring one long day week prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Momento, with the colors being as nearly true as possible with illustrations of this type. Sheet 1 is a color photograph of Momento grown as a single stem cut spray mum. Sheet 2 is a black and white photograph of three views of the inflorescence of Momento. Sheet 3 is a black and white photograph showing the upper and under sides of the leaves of Momento at three stages of development (mature, intermediate and immature).

Of the commercial cultivars known to the inventor, the most similar in comparison to Momento is the unpatented cultivar identified as Golden Polaris. Reference is made to attached Chart A, which compares certain characteristics of Momento to the same characteristics of Golden Polaris.

Similar traits are capitulum form and type, spray formation, plant height and low temperature tolerance. The ray floret color of Momento is a deeper, more clear yellow than the ray floret color of Golden Polaris. The peduncle length of the top terminal of Momento is slightly shorter than that of Golden Polaris. In addition, Momento has a smaller diameter of capitulum and a faster photoperiodic flowering response than Golden Polaris.

In the following description color references are made to The Royal Horticultural Society Color Chart.

The color values were determined on plant material grown in Salinas, Calif. on July 17, 1989.

Classification:

*Botanical.*—*Dendranthema grandiflora* cv Momento.

*Commercial.*—Decorative cut spray mum.

INFLORESCENCE

A. Capitulum:

*Form.*—Flat.

*Type.*—Decorative.

*Diameter across face.*—Up to 7 cm at maturity.

B. Corolla of ray florets:

*Color (general tonality from a distance of three meters).*—Yellow.

*Color (upper surface).*—Closest to 6A.

*Color (under surface).*—Closest to 6C.

*Shape.*—Straight, cross-section flat to slightly ribbed, apex convex.

C. Corolla of disc florets:

*Color (mature).*—Closest to 9A.

*Color (immature).*—Closest to 1A.

D. Reproductive organs:

*Androecium.*—Present on disc florets only; very few disc florets, not visible in the mature flower; scant pollen.

*Gynoecium.*—Present on both ray and disc florets.

PLANT

A. General Appearance:

*Height.*—Tall; 90 to 100 cm as a single stem cut mum with one long day week prior to short days.

B. Foliage:

*Color (upper surface).*—147A.

*Color (under surface).*—147B.

*Shape.*—Deeply lobed and serrated.

CHART A

COMPARISON OF MOMENTO AND GOLDEN POLARIS

| | MOMENTO | GOLDEN POLARIS |
|---|---|---|
| Ray floret color | Yellow | Yellow |
| Capitulum form and type | Flat decorative | Flat decorative |
| Spray formation | Terminal | Terminal |
| Peduncle length | 10 to 20 cm | 15 to 20 cm |
| Diameter across face of capitulum | Up to 7 cm | Up to 8 cm |
| plant height | Tall | Tall |
| Flowering response period | 8 weeks | 9 weeks |
| Low temperature tolerance | Excellent | Excellent |

Comparisons Made of Plants Grown As Single Stem Spray Cut Mums in Salinas, California

I claim:

1. A new and distinct Chrysanthemum plant named Momento, as described and illustrated.

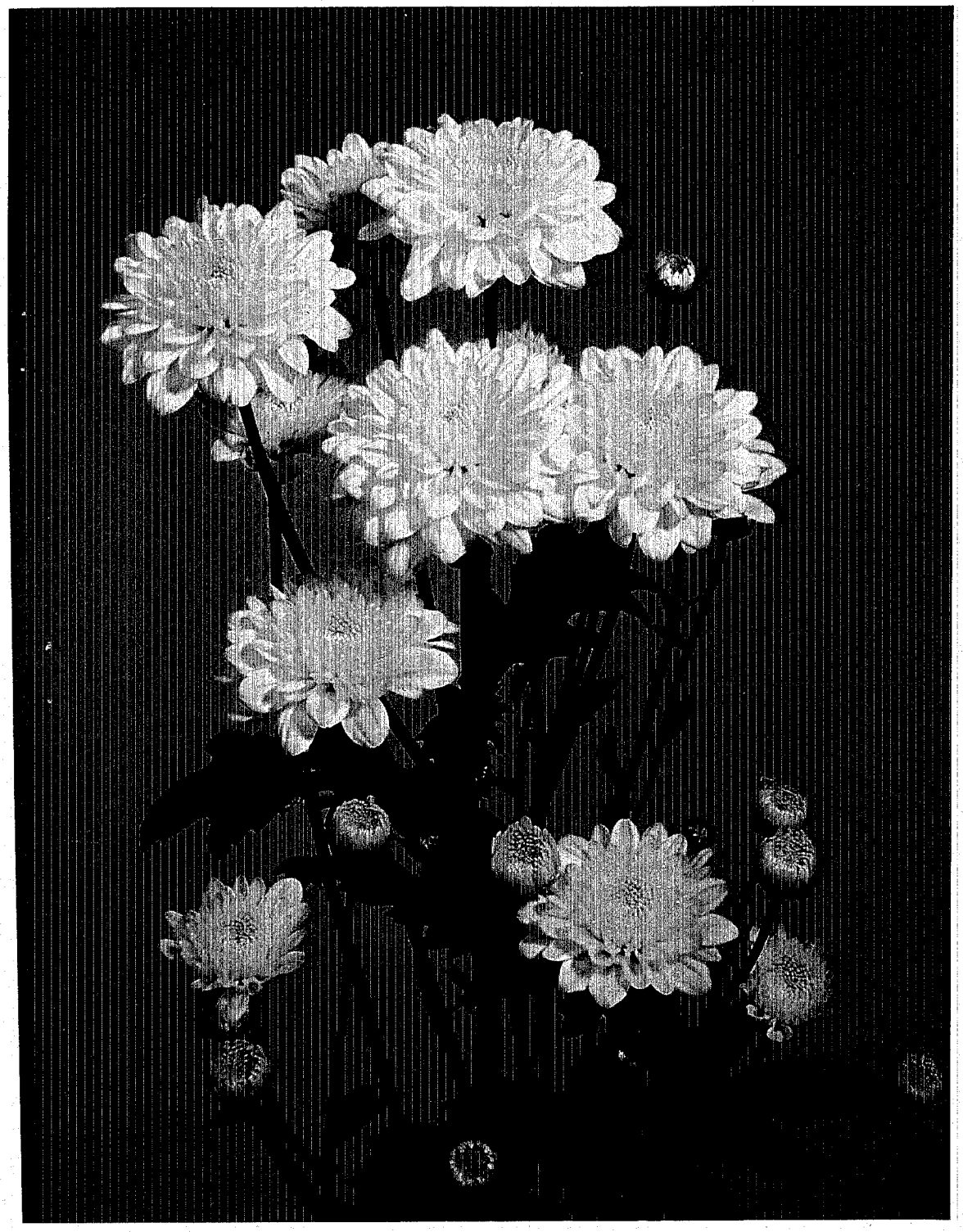

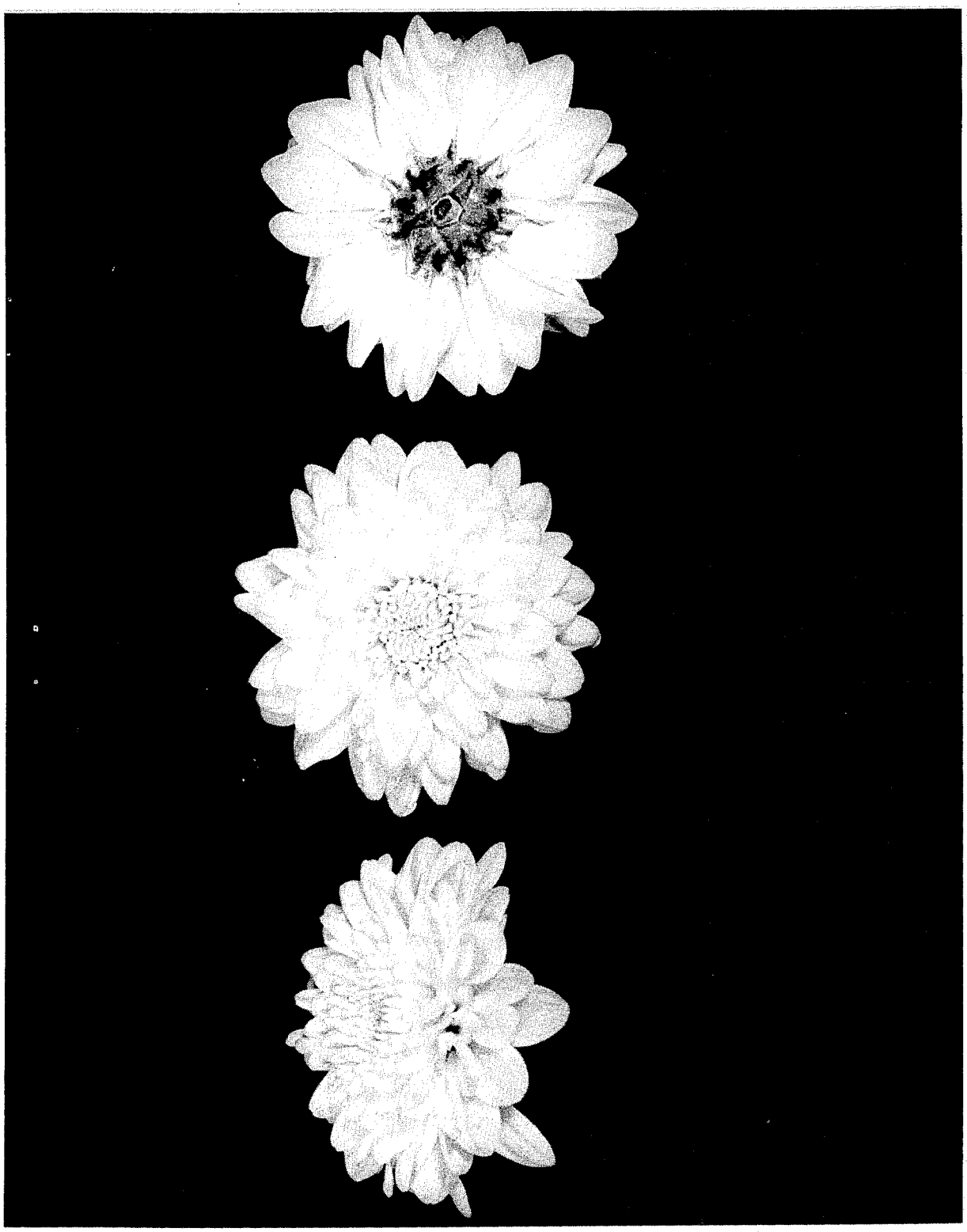

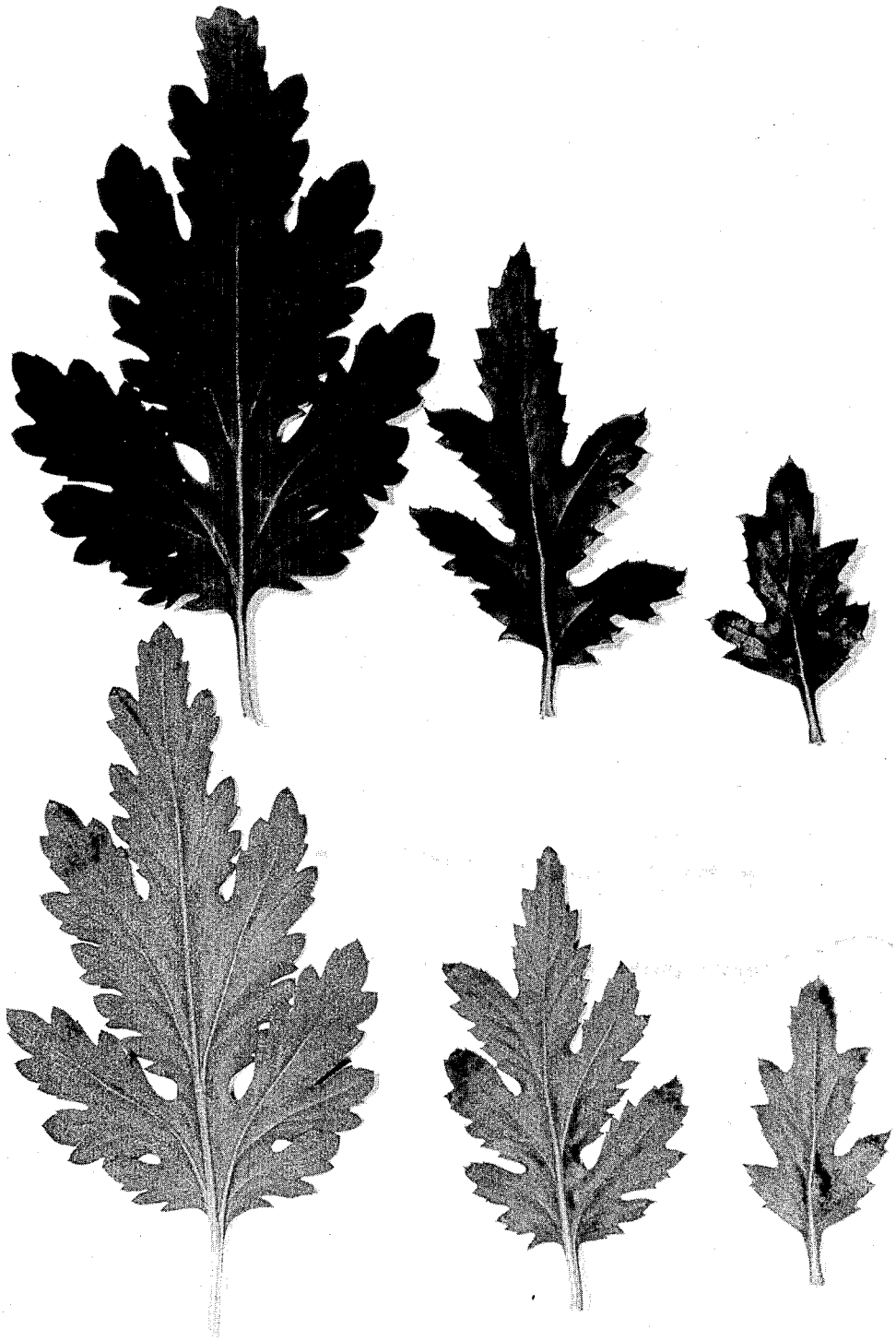

* * * * *